US008501975B2

(12) United States Patent
Kadyrov et al.

(10) Patent No.: US 8,501,975 B2
(45) Date of Patent: Aug. 6, 2013

(54) METHOD FOR MANUFACTURING RUTHENIUM CARBENE COMPLEXES

(75) Inventors: Renat Kadyrov, Frankfurt (DE); Anna Rosiak, Hannover (DE)

(73) Assignee: Evonik Degussa GmbH (DE)

( * ) Notice: Subject to any disclaimer, the term of this patent is extended or adjusted under 35 U.S.C. 154(b) by 242 days.

(21) Appl. No.: 12/937,046

(22) PCT Filed: Apr. 8, 2009

(86) PCT No.: PCT/EP2009/054248
§ 371 (c)(1),
(2), (4) Date: Nov. 2, 2010

(87) PCT Pub. No.: WO2009/124977
PCT Pub. Date: Oct. 15, 2009

(65) Prior Publication Data
US 2011/0040099 A1    Feb. 17, 2011

(30) Foreign Application Priority Data
Apr. 8, 2008 (DE) .......................... 10 2008 001 054

(51) Int. Cl.
*C07F 15/00* (2006.01)
(52) U.S. Cl.
USPC .................. 556/23; 549/3; 549/209
(58) Field of Classification Search
USPC ........................ 556/23; 549/3, 209
See application file for complete search history.

(56) References Cited

U.S. PATENT DOCUMENTS

| 5,912,376 A | 6/1999 | Van Der Schaaf et al. |
| 2006/0287450 A1 | 12/2006 | Kohler et al. |

FOREIGN PATENT DOCUMENTS

| CA | 2352377 A1 | 6/2000 |
| DE | 19854869 A1 | 5/2000 |
| EP | 0839821 A2 | 5/1998 |
| WO | WO-93/20111 A2 | 10/1993 |
| WO | WO-96/04289 A1 | 2/1996 |
| WO | WO-97/06185 A1 | 2/1997 |
| WO | WO-98/21214 A1 | 5/1998 |
| WO | WO 2005/016522 | * 2/2005 |
| WO | WO-2005/016522 A1 | 2/2005 |

OTHER PUBLICATIONS

European Office Action in corresponding European Application No. 09 730 836.5-2117 dated Jul. 10, 2012.
Schürer et al. "Synthese and Anwendung eines permanent immobilisierten Olefinmetathese-Katalysators", Angew. Chem., vol. 112, No. 21, pp. 4062-4065, 2000.
Frémont et al., "Ruthenium-indenylidene complexes in ring opening metathesis polymerization (ROMP) reactions", Journal of Molecular Catalysis, vol. 283, pp. 108-113, 2008.
Nguyen, S.T., "The designs, syntheses, and applications of well-defined, single component group VIII olefin metathesis catalysts," California Institute of Technology, Pasadena, 1995, p. 34, compound 11, Retrieved from the Internet: URL: http://resolver.caltech.edu/caltechETD:etd-09282005-160712.
Harlow, K.J., et al., "The first co-ordinatively unsaturated group 8 allenylidene complexes: insights into Grubbs' vs. Dixneuf-Furstner olefin metathesis catalysts," J. Chem. Soc., Dalton Trans., 1999, vol. 3, pp. 285-291.
Furstner, A., et al., "Indenylidene complexes of ruthenium: optimized synthesis, structure elucidation, and performance as catalysts for olefin metathesis-application to the synthesis of the ADE-ring system of nakadomarin A," Chem. Eur. J., 2007, vol. 7, No. 22, pp. 4811-4820.
Pierre De Frémont et al., "Ruthenium-indenylidene complexes in ring opening metathesis polymerization (ROMP) reactions", Journal of Molecular Catalysis A: Chemical, vol. 283, pp. 108-113, (2008).
U.S. Appl. No. 12/109,092, filed Apr. 24, 2009, Kadyrov.
U.S. Appl. No. 10/630,552, filed Jul. 30, 2003, Ehrlich.
U.S. Appl. No. 11/021,967, filed Dec. 23, 2004, Herrmann.
U.S. Appl. No. 11/828,828, filed Jul. 26, 2007, Herrmann.
U.S. Appl. No. 12/115,139, filed May 29, 2008, Iijima.
U.S. Appl. No. 12/478,317, filed Jun. 4, 2009, Herrmann.
U.S. Appl. No. 12/692,229, filed Jan. 22, 2010, Herrmann.
U.S. Appl. No. 09/488,630, filed Jan. 20, 2000, Herrmann.
U.S. Appl. No. 10/371,955, filed Feb. 20, 2003, Herrmann.
France, Marica Beth, "Olefin Metathesis with Group VIII Transition Metal Complexes: Mechanism, Reactivity, and Catalyst Development", Thesis, pp. 1-217, 1995.

\* cited by examiner

*Primary Examiner* — Joseph Kosack
(74) *Attorney, Agent, or Firm* — Novak Druce Connolly Bove + Quigg LLP

(57) ABSTRACT

A method of manufacturing ruthenium carbene complexes and novel aryl alkylidene ruthenium complexes based on the method, the complexes able to used as catalysts in metathesis reactions.

11 Claims, No Drawings

METHOD FOR MANUFACTURING RUTHENIUM CARBENE COMPLEXES

CROSS REFERENCE TO RELATED APPLICATION

This application is a national stage application (under 35 U.S.C. §371) of PCT/EP2009/054248, filed Apr. 8, 2008, which claims benefit of German application 102008001054.5, filed Apr. 8, 2008.

BACKGROUND OF THE INVENTION

The present invention relates to a process for preparing carbene-ruthenium complexes and also novel arylalkylidene-ruthenium complexes which can be prepared on the basis of this process and can be used, for example, as catalysts in metathesis reactions.

Increasing efforts have been made in recent years to prepare homogeneous catalysts which are both thermally stable and stable to water and air for olefin metathesis. Specific ruthenium-alkylidene compounds have attracted particular interest here.

Carbene-ruthenium complexes are extremely effective catalysts for olefin metathesis. Their unique properties, e.g. the high tolerance to water, air and polar functional groups, is the reason why they are used in organic synthesis to an ever increasing extent. The greatly increased demand and the manifold possible uses of these catalysts have inevitably led to a search for alternative synthetic routes.

Ruthenium metal-carbene complexes of the general structure $RuX_2(=CH-CH=CR_2)L_2$ for the metathesis polymerization of olefins are described, for example, in the patent applications WO 93/20111. Triphenylphosphane and substituted triphenylphosphane are used as ligands L. The complexes are prepared by reaction of $RuCl_2(PPh_3)_3$ with suitable disubstituted cyclopropenes as carbene precursors. However, the cyclopropenes are thermally unstable and are not commercially available. For this reason, they have to be prepared in a complicated process shortly before the synthesis.

Similar reactions with $[Ru(p-cymene)Cl]_2$ are described in WO 96/04289.

WO 97/06185 likewise describes metathesis catalysts based on ruthenium metal-carbene complexes. They can be prepared by reaction of $RuCl_2(PPh_3)_3$ with diazoalkanes.

However, handling diazoalkanes represents a safety risk, especially when carrying out the process on an industrial scale.

Hill et al. Dalton 1999, 285-291, describe the synthesis of Ru-indenylidene complexes from $RuCl_2(PPh_3)_3$ and diphenyl-propargyl alcohol.

Hoffmann et al. Journal of Organometallic Chemistry 641 (2002) 220-226, describe the synthesis of Ru-alkylidene complexes from the Wilkinson hydride complex RuHCl(PPh$_3$)$_3$.

For both processes, the organometallic starting material of the formula $RuCl_2(PPh_3)_3$ which is used has to be prepared from $RuCl_3$ using a large excess of triphenylphosphane ($PPh_3$). However, in the catalyst synthesis itself, $PPh_3$ ligands are lost again after the ligand exchange.

Grünwald et al. [Grünwald, C., Gevert, O., Wolf, J., Gonzàlez-Herrero, P., Werner, H., Organometallics 15 (1996), 1969-1962] describe a process for preparing ruthenium complexes in which polymeric $[RuCl_2(COD)]_n$ is reacted with hydrogen in i-propanol in the presence of phosphane.

These processes have the disadvantage that long reaction times and a two-fold excess of phosphane are required.

According to a method described in EP0839821, the reaction proceeds without hydrogen and less phosphane is needed. However, vinylidene complexes are often formed in this method of carrying out the reaction, as described, for example, by Ozawa [H. Katayama, F. Ozawa Organometallics 17 (1998), 5190-6].

WO 9821214 describes syntheses of carbene complexes which start out from the ruthenium polyhydride RuHCl(H$_2$)x(PCy$_3$)$_2$, where PCy$_3$ is tricyclohexylphosphane.

However, the ruthenium polyhydride complex is difficult to obtain. In addition, long reaction times are required.

The known synthetic routes for preparing metathesis catalysts of the type $RuX_2(=CH-R)(PR'_3)_2$ are uneconomical for the stated reasons.

The patent DE19854869 describes a one-pot synthesis of the carbene-ruthenium complexes $RuX_2(=CH-CH_2R)(PCy_3)_2$ from $RuCl_3$, Mg, $PCy_3$, hydrogen and acetylene.

However, handling acetylene represents a safety risk, particularly when carrying out the process on an industrial scale.

BRIEF SUMMARY OF THE INVENTION

It is an object of the invention to provide a process for preparing ruthenium-carbene complexes which is stable in industrial operation and should be superior to the known preparative processes of the prior art both from economic and ecological points of view.

This object is achieved by a process for preparing ruthenium complexes of the general formula

$$RuX_2(=CH-CH_2R)L_2 \qquad (1), \text{where}$$

X is an anionic ligand,
R is hydrogen or a $(C_1-C_{18})$-alkyl, $(C_3-C_8)$-cycloalkyl, $(C_2-C_7)$-heterocycloalkyl, $(C_6-C_{14})$-aryl or $(C_3-C_{14})$-heteroaryl radical and
L is an uncharged electron donor ligand, characterized in that
A) an Ru metal salt of the general formula:

$$RuX_xN_y \qquad (II), \text{where}$$

x is an integer greater than or equal to 2 and
X is as defined above,
y is an integer greater than or equal to 0
and for y>=1
the ligands N are identical or different coordinating uncharged ligands;
is reacted with L in the presence of a base and reducing agents and
B) subsequently reacted with a silylalkyne of the general formula III

$$R-C\equiv CSiR'_3 \qquad (III), \text{where}$$

R is as defined above,
the radicals R' are identical or different radicals which can be selected from the group consisting of hydrogen, $(C_1-C_8)$-alkyl, $(C_1-C_8)$-alkoxy, $(C_6-C_{10})$-aryloxy, $(C_6-C_{10})$-aryl.

DETAILED DESCRIPTION OF THE INVENTION

In a preferred embodiment the two anionic ligands X are identical and the two uncharged electron donor ligands L are likewise identical.

R is preferably hydrogen or a substituted $(C_1-C_{12})$-alkyl radical or a substituted $(C_6-C_{10})$-aryl radical.

R is particularly preferably hydrogen.

The object of the invention is likewise achieved by a process for preparing ruthenium complexes of the general formula $$RuX_2(=CR^1R^2)L_2, \text{ where}$$

X and L have the meanings given above and
$R^1$ is hydrogen or a $(C_1-C_{18})$-alkyl, $(C_3-C_8)$-cycloalkyl, $(C_2-C_7)$-heterocycloalkyl, $(C_6-C_{14})$-aryl or $(C_3-C_{14})$-heteroaryl radical and $R^2$ is a $(C_6-C_{14})$-aryl or $(C_3-C_{14})$-heteroaryl radical and the radicals $R^1$ and $R^2$ can have a 5-7-membered ring, characterized in that
A) an Ru metal salt of the general formula:

$$RuX_xN_y \quad \text{(II), where}$$

X, N and the integers x and y have the meanings given above; is reacted with L in the presence of a base and reducing agents and
B) subsequently reacted with a silylalkyne of the general formula III $$R—C\equiv CSiR'_3 \quad \text{(III), where}$$

R and R' have the meanings given above, and
C) subsequently reacted with an alkene of the general formula IV $$H_2C=CR^1R^2 \quad \text{(IV), where}$$

$R^1$ and $R^2$ have the meanings given above.
Preference is given to $R^1$ being hydrogen and $R^2$ being a substituted $(C_6-C_{10})$-aryl radical or a substituted $(C_3-C_{10})$-heteroaryl radical.

The uncharged electron donor ligand L can be selected from the group consisting of phosphanes, phosphinites, phosphonites and phosphites.

The ligand L can advantageously be selected from the group consisting of triphenylphosphane, triisopropyl-phosphane, tricyclohexylphosphane and 9-cyclo-hexyl-9-phosphabicyclo[3.3.1]nonane.

The ligand $L_2$ can be selected from the group consisting of bidentate ligands of the general formula

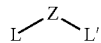

where
L and L' are identical or different selected from the group consisting of —$PR^1R^2$, —$P(OR^1)(OR^2)$, —$NR^1R^2$ and heterocyclic carbene, and Z is a bridge which covalently links the two groups.

The reduction of the Ru metal salt of the general formula $RuX_xN_y$ can be carried out by means of hydrogen in the presence of metallic reducing agent if x=3 and y=0. In this case, it is possible to use e.g. magnesium as reducing agent.

As base, it is possible to use an excess of basic ligand.
The reaction B) can be carried out in the presence of water.
The reduction of Ru metal salts of the general formula $RuX_xN_y$ can be carried out by means of alcohol or the formic acid-triethylamine complex if x>=2 and y>0. In this case, the reducing agent used is preferably secondary alcohol.

As base, it is possible to use an amine.
It is also possible to use triethylamine or 1,8-diazo-bicyclo[5.4.0]undec-7-ene as base.

X can be a monovalent anionic ligand or $X_2$ can be a single divalent anionic ligand, for example halogen, pseudohalogen, carboxylate, sulphate or diketonate. X is preferably a halogen, in particular bromine or chlorine, especially chlorine.

The invention further provides Ru-carbene complexes of the general formula (VI)

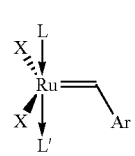

where L and L' are identical or different and are each an uncharged electron donor, X is an anionic ligand, Ar is a naphthyl radical or a $(C_3-C_{14})$-heteroaryl radical, where Ar may be substituted.

L and L' can be selected independently from the group consisting of triphenylphosphane, triisopropylphosphane, tricyclohexylphosphane and 9-cyclohexyl-9-phospha-bicyclo[3.3.1]nonane.

L can be a heterocyclic carbene and L' can be selected from the group consisting of triphenylphosphane, triisopropylphosphane, tricyclohexylphosphane and 9-cyclohexyl-9-phosphabicyclo[3.3.1]nonane.

Ar is preferably a furyl or thienyl radical.
These Ru-carbene complexes can be used in metathesis reactions.

The desired ruthenium complexes of the formula I $$RuX_2(=CH—CH_2R)L_2 \quad \text{(I),}$$

where X is an anionic ligand, R is hydrogen or a substituted or unsubstituted $(C_1-C_{18})$-alkyl or $(C_3-C_8)$-cycloalkyl or $(C_2-C_7)$-heterocycloalkyl, $(C_6-C_{14})$-aryl or $(C_3-C_{14})$-heteroaryl radical and the ligands L are uncharged electron donor ligands, are prepared in the process of the invention by firstly reacting a metal salt of the formula II:

$$RuX_xN_y \quad \text{(II),}$$

where X is as defined above, x is an integer greater than or equal to 2 and y is an integer greater than or equal to 0 and in the case of y>=1, the ligands N are identical or different coordinating uncharged ligands;
with L in the presence of a base and a reducing agent and in the presence or absence of hydrogen (reaction A) and subsequently, without isolation of the intermediates, with a silylalkyne of the general formula III $$R—C\equiv CSiR'_3 \quad \text{(III),}$$

where R is as defined above and the radicals R' are identical or different radicals which can be selected from the group consisting of hydrogen, $(C_1-C_8)$-alkyl, $(C_1-C_8)$-alkoxy, $(C_6-C_{10})$-aryloxy, $(C_6-C_{10})$-aryl, in the presence of an acid (reaction B).

As reducing agent, it is possible to use any reducing agent, with preference being given to hydrogen, formic acid, alcohols and metallic reducing agents. Particular preference is given to hydrogen, secondary alcohols and alkaline earth metals.

The reduction of RuX3 (formula II; x=3, y=0) can preferably be carried out by means of hydrogen in the presence of a metallic reducing agent, preferably in the presence of an alkali metal, alkaline earth metal or transition metal such as zinc, which is present in metallic form.

The alkaline earth metals, preferably magnesium, are preferably used in an activated form. Here, the activation can be carried out, for example, by contacting with a chloroalkane or bromoalkane.

For example, in a one-pot reaction, magnesium can be placed in a dilute chlorine-containing organic solvent, for example dichloroethane, under an inert gas atmosphere and, after an activation reaction, reacted for preferably from one minute to one hour with the solvent, RuX3 and the ligand L under a hydrogen atmosphere.

In this embodiment, the role of the base can be performed by an excess of basic ligand L.

Here, the molar ratio of ligand L to ruthenium salt used is preferably 3-10:1, particularly preferably 3-5:1.

The reaction of RuX3 or its hydrate with the ligand L is firstly carried out in an inert solvent in the presence of a reducing agent and of hydrogen.

The temperature in this reaction step can be from 0 to 100° C., preferably from 40 to 80° C.

The pressure can be preferably from 0.01 to 100 bar, particularly preferably from 0.01 to 5 bar, in particular from 0.01 to 1 bar.

As solvent, it is possible to use, for example, aromatics, heteroaromatics, cyclic or acyclic ethers.

Preferred solvents are toluene, N-methyl-2-pyrrolidone (NMP), tetrahydrofuran, dialkyl ether, glycol ethers and dioxane. Particular preference is given to tetrahydrofuran.

The reduction of $RuX_xN_y$ (formula II; $x>=2$, $y>=1$) can preferably be carried out by means of an alcohol, preferably a secondary or tertiary alcohol such as isopropanol or tert-butyl alcohol, or by means of formic acid or a derivative thereof, e.g. the formic acid-triethylamine complex.

The process of the invention is advantageously carried out by suspending a metal salt ($RuX_xN_y$) of the formula II, a base and a ligand and, if appropriate, a reducing agent, preferably formic acid, in an alcohol and/or inert solvent.

As bases, it is possible to use any inorganic and organic base, preferably a nitrogen base, or basic ligand L. The temperature in this step is preferably from 0 to 150° C., particularly preferably from 20 to 100° C., in particular from 40 to 80° C.

The reaction mixture in the reaction B is subsequently reacted with a silylalkyne of the general formula (II) at a temperature preferably in the range from −80 to 60° C., particularly preferably from −30 to 20° C. Here, the molar ratio of ruthenium salt originally used to silylalkyne can preferably be from 1:1 to 1:4.

The reaction is preferably carried out in the presence of an acid.

As acids, it is possible to use Brønsted acids, e.g. mineral acids, or water. In the latter case, the acid is generated "in-situ" from the water and salt.

It is advantageous to carry out the subsequent reaction (C) with compounds of the general formula:

where $R^1$ is hydrogen or a substituted or unsubstituted ($C_1$-$C_{18}$)-alkyl or ($C_3$-$C_8$)-cycloalkyl, ($C_2$-$C_7$)-heterocyclo-alkyl, ($C_6$-$C_{14}$)-aryl or ($C_3$-$C_{14}$)-heteroaryl radical, and $R^2$ is a ($C_6$-$C_{14}$)-aryl or ($C_3$-$C_{14}$)-heteroaryl radical and the radicals $R^1$ and $R^2$ may have a 5-7-membered ring; to give the more stable Ru-arylalkylidene complex of the general formula:

where X, L, $R^1$ and $R^2$ are as defined above, without isolation of ruthenium-alkylidene complexes (I).

In the process of the invention, it can be advantageous for the reaction B with silylalkyne to be followed immediately by addition of an alkene (V) to the resulting solution; the reaction temperature for this step is advantageously kept in the range from −50° C. to 40° C., preferably from −20° C. to 30° C. and particularly preferably from −10° C. to 20° C.

The reaction can preferably be carried out over a period of from 10 minutes to 48 hours, particularly preferably from 30 minutes to 10 hours.

The molar ratio of alkene (IV) to the ruthenium salt originally used can preferably be 1-20:1, particularly preferably 2-10:1.

The invention further provides Ru-carbene complexes of the general formula (VI) which have been made available for the first time by means of the present invention,

where L and L' are identical or different and are each an uncharged electron donor, X is an anionic ligand, Ar is a substituted or unsubstituted naphthyl radical or a ($C_3$-$C_{14}$)-heteroaryl radical.

L and L' can preferably be selected independently from the group consisting of triphenylphosphane, triisopropylphosphane, tricyclohexylphosphane and 9-cyclohexyl-9-phosphabicyclo[3.3.1]nonane.

L can preferably be a heterocyclic carbene and L' is selected from the group consisting of triphenylphosphane, triisopropylphosphane, tricyclohexylphosphane and 9-cyclohexyl-9-phosphabicyclo[3.3.1]nonane.

The novel Ru-carbene complexes of the formula VI display a high catalytic activity in the metathesis reaction at room temperature combined with a remarkable thermal stability.

For the complex compounds of the formula VI according to the invention having two phosphanes as ligands L and L', high stability in the organic solvents is particularly advantageous when preparing complex compounds of the formula VI having N-heterocyclic carbenes as ligands.

The compounds prepared by the process of the invention are extraordinarily well suited as catalysts in the polymerization of cyclic olefins, in the cross-metathesis of various olefins and the ring closing metathesis (RCM) of dienes.

X can be a monovalent anionic ligand or $X_2$ can be a single divalent anionic ligand, for example halogen, pseudo-halogen, carboxylate, sulphate or diketonate. X can preferably be halogen, in particular bromine or chlorine, especially chlorine.

The ligands L are uncharged electron donor ligands. Examples are heterocyclic carbenes, amines, phosphanes, phosphonites, phosphinites, phosphites and arsanes, preferably phosphanes. Particular preference is given to triphenylphosphane, triisopropylphosphane and tricyclo-hexylphosphane.

In the process of the invention, it can be advantageous to use the ligands $L_2$ as chelating bidentate ligands. Examples are diphosphanes and diphosphites.

In the case of the chelating ligand $L_2$, it can also be advantageous to use a bidentate ligand having different coordinating groups L-Z-L'. Examples are aminophosphanes (VII), phosphane-phosphites (VIII) and carbene-phosphanes (IX):

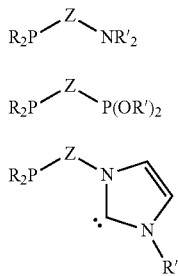

(VII)

(VIII)

(IX)

where Z is a bridge which covalently links the two coordinating groups L and L'.

For the purposes of the present invention, any base (proton acceptor) and any acid (proton donor) are suitable. Preferred bases are those which have a stronger basicity than water. Examples are nitrogen bases, metal hydroxides, metal alkoxides and phenoxides. Preferred bases are pyridine, triethylamine, 1,8-diazabicyclo[5.4.0]undec-7-ene, KOH, NaOH, KO-t-butyl and NaO-methyl, in particular triethylamine and 1,8-diazabicyclo[5.4.0]undec-7-ene (DBU). Preferred acids are Bronsted acids, particularly preferably hydrohalic acids. Examples are selected from the group consisting of HF, HCl, HBr and HI, with particular preference being given to HCl and HBr.

For the purposes of the present invention, an uncharged ligand N is a $(C_2-C_{12})$-alkene, $(C_3-C_{12})$-cycloalkene, $(C_6-C_{14})$-arene, $(C_3-C_{12})$-heteroarene, an ether, a phosphane, a phosphite, an amine, an imine, a nitrile, an isonitrile, a dialkylsulphoxide or water.

Examples of cycloalkenes are cyclopentene, cyclohexene, cycloheptene, cyclooctene, cyclododecene, cyclohexadiene, cycloheptadiene and the isomers of cyclooctadiene and cyclooctatetraene, bicyclo[2.2.1]hepta-2,5-diene.

Arenes and heteroarenes are, for example, benzene, p-cymene, biphenyl, naphthalene, anthracene, acenaphthene, fluorene, phenanthrene, furan, thiophene, coumarone, thionaphthene, dibenzofuran, dibenzothiophene, chromene or thianthrene.

The nitrogen bases are, for example, amines, nitrogen aromatics or guanidines.

Examples of amines are ammonia, triethylamine, N,N-dimethylaniline, piperidine, N-methylpyrrolidine, 1,4-diazabicyclo[2.2.2]octane or 1,8-diazo-bicyclo[5.4.0]undec-7-ene.

The nitrogen aromatics are, for example, pyridine, pyrimidine, pyrazine, pyrrole, indole, carbazole, imidazole, pyrazole, benzimidazole, oxazole, thiazole, isoxazole, isothiazole, quinoline, isoquinoline, acridine, phenazine, phenoxazine, phenothiazine or triazine.

Examples of guanidines are 1,1,3,3-tetramethylguanidine and 1,3-dimethylimidazolidin-2-imine.

Imines are a group of chemical compounds in which the oxygen atom of an aldehyde or ketone has been replaced by a nitrogen atom. The nitrogen atom additionally bears a hydrogen or another organic radical.

Examples of nitriles are acetonitrile and benzonitrile. Examples of isonitriles are n-butyl isonitrile, cyclohexyl isonitrile and benzyl isonitrile.

Examples of ethers are dibutyl ether, tetrahydrofuran, dioxane, ethylene glycol monomethyl or dimethyl ether, ethylene glycol monoethyl or diethyl ether, diethylene glycol diethyl ether and triethylene glycol dimethyl ether. Examples of dialkyl sulphoxides are dimethyl sulphoxide, tetramethylene and pentamethylene sulphoxide.

For the purposes of the present invention, phosphanes are compounds of the formula $PR^1R^2R^3$, wherein $R^1$, $R^2$ and $R^3$ can be identical or different and can be selected from the group consisting of hydrogen, $(C_1-C_{18})$-alkyl, $(C_3-C_8)$-cycloalkyl, $(C_2-C_7)$-heterocycloalkyl, $(C_6-C_{14})$-aryl and $(C_3-C_{14})$-heteroaryl, where the radicals $R^1$, $R^2$ and $R^3$ may have one or more cyclic structures.

For the purposes of the present invention, phosphinites are compounds of the formula $PR^1R^2R^3$, where $R^1$, $R^2$ can be identical or different and can be selected from the group consisting of $(C_1-C_{18})$-alkyl, $(C_3-C_8)$-cycloalkyl, $(C_2-C_7)$-heterocycloalkyl, $(C_6-C_{14})$-aryl and $(C_3-C_{14})$-heteroaryl and $R^3$ can be selected from the group consisting of —OH, $(C_1-C_8)$-alkoxy, $(C_6-C_{14})$-aryloxy, where the radicals $R^1$, $R^2$ and $R^3$ may have one or more cyclic structures.

For the purposes of the present invention, phosphonites are compounds of the formula $PR^1R^2R^3$, where $R^1$, $R^2$ can be identical or different and can be selected from the group consisting of $(C_1-C_8)$-alkoxy, $(C_6-C_{14})$-aryloxy and $R^3$ can be selected from the group consisting of $(C_1-C_{18})$-alkyl, $(C_3-C_8)$-cycloalkyl, $(C_2-C_7)$-heterocycloalkyl, $(C_6-C_{14})$-aryl and $(C_3-C_{14})$-hetero-aryl, where the radicals $R^1$, $R^2$ and $R^3$ may have one or more cyclic structures.

For the purposes of the present invention, phosphites are compounds of the formula $PR^1R^2R^3$, where $R^1$, $R^2$ and $R^3$ can be identical or different and can be selected from the group consisting of —OH, $(C_1-C_8)$-alkoxy, $(C_6-C_{14})$-aryloxy, where the radicals $R^1$, $R^2$ and $R^3$ may have one or more cyclic structures.

$(C_1-C_{18})$-Alkyl radicals are methyl, ethyl, n-propyl, isopropyl, n-butyl, isobutyl, sec-butyl, tert-butyl, pentyl, hexyl, heptyl, octyl, nonanyl, decanyl, dodecanyl, and octadecanyl, including all their structural isomers. The radical $(C_1-C_{18})$-alkoxy corresponds to the radical $(C_1-C_{18})$-alkyl with the proviso that it is bound to the molecule via an oxygen atom.

The term $(C_3-C_8)$-cycloalkyl refers to cyclopropyl, cyclobutyl, cyclopentyl, cyclohexyl and cycloheptyl radicals etc. These can be substituted by one or more halogens and/or N-, O-, P-, S-, Si-containing radicals and/or have N-, O-, P-, S atoms in the ring, e.g. 1-, 2-, 3-, 4-piperidyl, 1-, 2-, 3-pyrrolidinyl, 2-, 3-tetrahydrofuryl, 2-, 3-, 4-morpholinyl.

The term $(C_6-C_{14})$-aryl radical refers to an aromatic radical having from 6 to 14 carbon atoms. Such radicals include, in particular, compounds such as phenyl, naphthyl, anthryl, phenanthryl, biphenyl radicals or systems fused onto the molecule concerned in the above-described manner, e.g. indenyl systems, which may be substituted by halogen, $(C_1-C_8)$-alkyl, $(C_1-C_8)$-alkoxy, $NH_2$, —NO, —$NO_2$, $NH(C_1-C_8)$-alkyl, —$N((C_1-C_8)$-alkyl$)_2$, —OH, —$CF_3$, —$C_nF_{2n+1}$, $NH(C_1-C_8)$-acyl, $N((C_1-C_8)$-acyl$)_2$, $(C_1-C_8)$-acyl, $(C_1-C_8)$-acyloxy, —$S(O)_2((C_1-C_8)$-alkoxy), —$S(O)((C_1-C_8)$-alkoxy), —$P(O)((C_1-C_8)$-alkoxy$)_2$ or —$OP(O)((C_1-C_8)$-alkoxy$)_2$.

For the purposes of the present invention, a $(C_3-C_{14})$-heteroaryl radical is a five-, six- or seven-membered aromatic ring system which has from 3 to 14 carbon atoms and has heteroatoms such as nitrogen, oxygen or sulphur in the ring.

Such heteroaromatics are, in particular, radicals such as 1-, 2-, 3-furyl, 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl, 2-, 4-, 5-, 6-pyrimidinyl. This radical can be substituted by the same radicals as the abovementioned aryl radical.

A heterocyclic carbene is a carbene of one of the general formulae

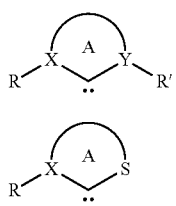

where R and R' can be identical or different and can be selected from the group consisting of hydrogen, $(C_1-C_{18})$-alkyl, $(C_3-C_8)$-cycloalkyl, $(C_2-C_7)$-heterocycloalkyl, $(C_6-C_{14})$-aryl and $(C_3-C_{14})$-heteroaryl, X and Y can each be, independently of one another, a nitrogen or phosphorus atom and A can be part of a $C_2-C_4$ bridge (saturated or unsaturated, substituted or unsubstituted, with bridge carbons being able to be substituted by heteroatoms).

Possible halogens are fluorine, chlorine, bromine and iodine.

The references mentioned in this text are hereby incorporated by reference into the present disclosure.

In the group $C_nF_{2n+1}$, n is an integer from 2 to 5.

Organosilyl groups are R', R" R'" Si radicals, where R', R" and R'" can be selected independently from the group consisting of hydrogen, $(C_1-C_8)$-alkyl, $(C_6-C_{18})$-aryl, $(C_1-C_8)$-alkoxy, $(C_6-C_{18})$-aryloxy.

The processes of the invention have the advantage that the desired ruthenium-alkylidene complexes can be synthesized using readily available Ru salts and a silylalkyne and, if appropriate, an alkene.

The process can be carried out at atmospheric pressure and in industrial solvents. In addition, no thermally unstable cyclopropene or diazoalkane compounds are used.

Compared to the known method described in DE19854869, less phosphine is required.

In addition, the acetylene used in DE19854869 is replaced by the less hazardous and more readily meterable trimethylsilylacetylene. Furthermore, the total yield is higher.

In contrast to the known method described in EP0839821, little or no vinylidene complex formation is generally observed. The latter complexes are difficult to separate from the desired alkylidene complexes and do not exchange the carbene unit under mild reaction conditions. They are consequently very sluggish metathesis catalysts. The ruthenium complexes in this process do not contain any heteroatoms on the carbene carbon.

Example 1

Synthesis of the Ethylidene Complex

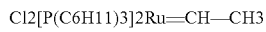

a) A suspension of 2.7 g of Mg in 100 ml of THF was admixed with 2.8 ml of 1,2-dichloroethane. After the vigorous reaction was complete, 2.43 g of ruthenium chloride hydrate and 8.4 g of tricyclohexylphosphane were added, after stirring for 10 minutes the protective gas was replaced by hydrogen having a gauge pressure of 0.01 bar and the reaction mixture was heated at 60° C. in the closed flask for 4 hours. The resulting orange suspension was cooled to −40° C. and, after addition of 1.4 ml of trimethylsilylacetylene, warmed to 5° C. over a period of 30 minutes. 0.6 ml of water was subsequently added and the mixture was stirred at 0° C. for another 30 minutes. The mixture was filtered to remove excess magnesium and the filtrate was evaporated at 0° C. under reduced pressure. The residue was stirred with cold MeOH. The resulting violet powder was washed with cold methanol and dried under reduced pressure. Yield 7.23 g (95%).

NMR in CDCl3 δ $^{31}$P 35.8; H δ 19.30 (q, J=5.6, 1H), 2.60 (d, J=5.5, 3H), 2.60-2.52 (m, 6H), 1.88-1.22 (m, 60H).

b) A brown suspension of RuCl2(1,5-cyclooctadiene) (560 mg; 2 mmol), 0.6 ml of 1,8-diazobicyclo[5.4.0]undec-7-ene (DBU) and 1.18 g of tricyclohexylphosphine in 60 ml of isopropanol was stirred at 80° C. for 2 hours. 60 ml of toluene was added to the resulting brick-red suspension and the mixture was stirred at 80° C. for a further 90 minutes and cooled to −10° C. After addition of 0.55 ml of trimethylsilylacetylene, 10 ml of 2 M HCl solution in diethyl ether were added and the mixture was subsequently stirred for 5 minutes. The mixture was warmed while stirring to 0° C. and stirred for 45 minutes. After evaporation at 0° C. in a high vacuum, the residue was stirred with cold MeOH. The resulting violet powder was washed with cold methanol and dried under reduced pressure. Yield 1.40 g (92%).

Example 2

Synthesis of the Alkylidene Complex (2)

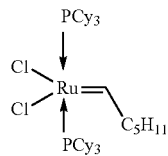

Ru(cod)Cl$_2$ (660 mg, 2.35 mmol) was suspended in iPrOH (20 ml) under an Ar atmosphere. DBU (0.75 ml) and PCy$_3$ solution (c=20%, 0.77 M in toluene, 7.7 ml) was added. The brown suspension obtained was stirred at 80° C. for 1 hour and toluene (25 ml) was then added. The mixture was stirred at 80° C. for a further 30 minutes. The reaction mixture was then cooled to 0° C. and 1-trimethylsilyl-1-hexyne (2.1 g) was added. After stirring for 10 minutes, HCl solution (c=2 M in Et$_2$O, 2.4 ml) was added to the reaction mixture at 0° C. After stirring for 1 hour, the reaction mixture was evaporated. MeOH (about 30 ml) was added to the residue. Filtration gave the complex 2. The NMR also shows by-products.

NMR in CDCl$_3$ δ $^{31}$P 35.81 ppm. $^1$H δ 20.01 ppm.

Example 3

Synthesis of the Benzylidene Complex

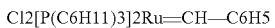

A suspension of 12 g of Mg in 100 ml of THF was admixed with 8 ml of 1,2-dichloroethane. After the vigorous reaction was complete, a solution of 12.2 g of ruthenium chloride hydrate and 42 g of tricyclohexylphosphane in 400 ml of THF was added, after stirring for 10 minutes the protective gas was replaced by hydrogen having a gauge pressure of 0.01 bar and the reaction mixture was heated to 60° C. in the closed flask for 5 hours. The resulting orange suspension was cooled to −40° C. and, after addition of 9.7 ml of trimethylsilylacetylene, warmed to 5° C. over a period of 30 minutes. 1.8 ml of water were subsequently added and the mixture was stirred at 0° C. for another 30 minutes. 11.5 ml of styrene were added to the resulting reaction mixture. After stirring for 1 hour at room temperature, the mixture was filtered and the filtrate was evaporated under reduced pressure. The residue was stirred with cold MeOH. The resulting violet powder was washed with cold methanol and dried under reduced pressure. Yield 37.44 g (91%).

Example 4

Preparation of dichlorobis(tricyclohexylphosphane)(thien-2-ylmethylidene)ruthenium(II) (4)

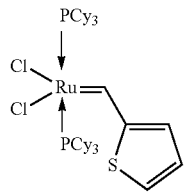

a) Ru(cod)Cl$_2$ (660 mg, 2.35 mmol) was suspended in iPrOH (20 ml) under an Ar atmosphere. DBU (0.75 ml, 5 mmol) and PCy$_3$ solution (c=20%, 0.77 M in toluene, 7.5 ml) were added. The brown suspension obtained was stirred at 80° C. for 1 hour. THF (30 ml) was then added and the mixture was stirred at 80° C. for a further 30 minutes. The reaction mixture was then cooled to 20° C. and HCl solution (c=2 M in Et$_2$O, 2.4 ml) was added. After stirring for 5 minutes, trimethylsilylacetylene (1.4 ml, 20.4 mmol) was added to the reaction mixture at about 22° C. and the mixture was stirred for 20 minutes. A solution of 2-vinylthiophene (c=about 50% in THF, 2.4 g) was subsequently added. After stirring at room temperature for 70 minutes, the reaction mixture was evaporated on a rotary evaporator. The residue was dissolved in DCM (about 5 ml). After addition of MeOH (40 ml), the suspension obtained was stirred under an Ar atmosphere for about 15 minutes. Filtration gave the complex 4 (1.15 g, 1.38 mmol, 59%) as a deep violet solid.

NMR in CDCl$_3$ δ $^{31}$P 35.96 ppm; $^1$H δ 19.11 (s, 1H), 8.20 (s, br., 1H), 7.87 (s, br., 1H), 6.97 (t, J=4.3 Hz, 1H), 2.64 (m, 6H), 1.81-1.67 (m, 33H), 1.48-1.41 (m, 12H), 1.27-1.14 (m, 21H) ppm. IR (ATR)λ$^{-1}$=2919 (vs), 2848 (s), 2169 (w), 2051 (w), 1936 (w), 1901 (w), 1443 (m), 1403 (m), 1353 (m), 1263 (m), 1005 (m), 734 (vs) cm$^{-1}$. MS (ESI) m/e=828 (21) [M$^+$], 793 (9), 281 (100).

b) A solution of 2-vinylthiophene (c=about 50% in THF, 2.4 g) was added to a solution of Cl$_2$[P(C$_6$H$_{11}$)$_3$]$_2$Ru=CH—CH$_3$ (1) (225 mg, 0.296 mmol) in toluene (5 ml). The reaction mixture was stirred at room temperature for 2 hours and the solvent was subsequently removed under reduced pressure. The residue was taken up in CH$_2$Cl$_2$ (about 1 ml) and precipitated by means of MeOH (about 10 ml). Filtration and washing with MeOH (about 3 ml) gave the product 4 (170 mg, 0.21 mmol, 71%) as a deep violet solid.

Example 5

Preparation of dichlorobis(tricyclohexylphosphane)(2-naphthylmethylidene)ruthenium(II) (5)

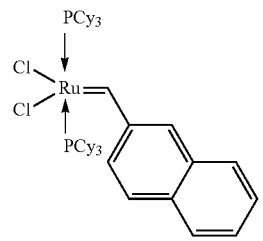

a) Ru(cod)Cl$_2$ (1.32 g, 4.71 mmol) was suspended in 50 ml of isopropanol under an Ar atmosphere. DBU (1.5 ml, 10 mmol) and PCy$_3$ solution (c=20%, 0.77 M in toluene, 15 ml, 11.6 mmol) were added. The brown suspension obtained was stirred at 80° C. for 1 hour. 60 ml of toluene was added to the resulting brick-red suspension and the mixture was stirred at 80° C. for a further 90 minutes. The reaction mixture was cooled to 5° C. and trimethylsilylacetylene (2.8 ml, 20.4 mmol) was added. After stirring for 5 minutes, 4.8 ml of 2 M HCl solution (9.6 mmol) in diethyl ether was added and the mixture was stirred for 20 minutes. A solution of 2-vinylnaphthalene (1 g, 6.5 mmol) in toluene (4.5 ml) was subsequently added. After stirring at room temperature for 120 minutes, the reaction mixture was evaporated on a rotary evaporator. The residue was taken up in dichloromethane (about 7 ml). After addition of MeOH (120 ml), the suspension obtained was stirred for about 15 minutes and cooled to −78° C. Filtration gave the complex (1.75 g, 43%) as a violet solid.

NMR in CDCl$_3$ δ $^{31}$P 37.43 ppm; $^1$H δ 20.12 (s, 1H), 8.82 (s, br., 1H), 8.77 (d, J=8.5 Hz, 1H), 8.06 (d, J=8.1 Hz, 1H), 7.74 (d, J=8.1 Hz, 1H), 7.71 (d, J=8.4 Hz, 1H), 7.67-7.63 (m, 1H), 7.46-7.42 (m, 1H), 2.63 (m, 6H), 1.90-1.60 (m, 33H), 1.46-1.37 (m, 12H), 1.30-1.10 (m, 21H) ppm. IR (ATR)λ$^{-1}$=2922 (vs), 2848 (s), 2358 (w), 2003 (w), 1443 (m), 1265 (m), 1004 (m), 733 (vs) cm$^{-1}$.

b) A solution of 2-vinylnaphthalene (154 mg, 1 mmol) in toluene (2 ml) was added to a solution of Cl$_2$[P(C$_6$H$_{11}$)$_3$]$_2$Ru=CH—CH$_3$ (1) (340 mg, 0.45 mmol) in toluene (5 ml) at −45° C. and under an argon atmosphere. The reaction mixture was stirred at room temperature for 2 hours. The solvent was subsequently distilled off under reduced pressure. The residue was taken up in CH$_2$Cl$_2$ (about 1 ml) and precipitated by means of MeOH (about 15 ml). The product 5, an intense violet solid, was filtered off and washed with MeOH (about 5 ml). Yield 220 mg (56%).

Example 6

Preparation of dichlorobis(2-naphthylmethylidene)(1,3-bis(2,4,6-trimethylphenyl)imidazol-2-yl](tricyclohexyl-phosphane)ruthenium (II) (6)

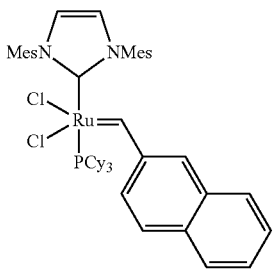

The 1,3-bis(2,4,6-trimethylphenyl)imidazolin-2-ylidene solution (1.08 mmol in 4 ml of toluene) was added to a solution of complex 5 (873 mg, 1 mmol) in toluene (20 ml) under an argon atmosphere. The reaction mixture was stirred at room temperature for 2 hours and subsequently washed with water (2×10 ml). The organic phase was evaporated. The residue was taken up in 1 ml of CH2Cl2, diluted with 10 ml of MeOH and cooled at −18° C. for 2 hours. Filtration gave the product 6 (300 mg, 0.33 mmol, 33%) as dark brown crystals.

NMR in CDCl$_3$ δ $^{31}$P 32.89 (br.) ppm; $^1$H δ=19.61 (s, 1H), 9.04 (s, br., 1H), 7.95 (d, J=7.7 Hz, 1H), 7.70 (d, J=7.8 Hz, 1H), 7.59 (t, br., J=6.8 Hz, 1H), 7.51 (d, J=8.8 Hz, 1H), 7.39 (t, br., J=7.3 Hz, 1H), 7.06 (s, br., 2H), 6.97 (m, 1H), 6.94 (m, 1H), 6.69 (s, br., 1H), 5.62 (br., 1H), 2.50 (m 6H), 2.36 (s, 3H), 2.0-0.94 39H) ppm. IR (ATR)λ=2923 (vs), 2849 (s), 1444 (m), 1388 (m), 1314 (m), 1262 (m), 1004 (w, br.), 843 (m), 732 (m) cm$^{-1}$. MS (ESI) m/e=896 (100) [M$^+$], 861 (3), 305 (43), 281 (31).

Example 7

Preparation of dichlorobis(2-naphthylmethylidene)[1,3-bis(2,4,6-trimethylphenyl)-4,5-dimethylimidazol-2-yl](tricyclohexylphosphane)ruthenium(II) (7)

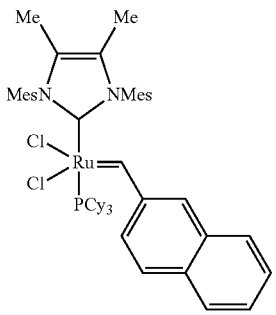

4,5-Dimethyl-1,3-bis(2,4,6-trimethylphenyl)imidazolin-2-ylidene (400 mg, 1.2 mmol) was added to a solution of complex 5 (873 mg, 1 mmol) in dried toluene (30 ml) and the mixture was stirred at room temperature under an argon atmosphere for 30 minutes. The reaction mixture was evaporated under reduced pressure and stirred with MeOH (15 ml). The precipitated crystals were filtered off and identified as starting complex 5. The filtrate was evaporated to half its volume and stored cold in a refrigerator. The dark brown-violet crystals of pure product 7 are filtered off and dried under reduced pressure.

NMR in CDCl$_3$ δ $^{31}$P 32.12 (br.) ppm; $^1$H δ=20.12 and 19.59 (s, 1H), 9.62 and 9.05 (br, 1H), 7.94 (d, J=8.0 Hz, 1H), 7.69 (d, J=8.0 Hz, 1H), 7.59 (t, br., J=7.0 Hz, 1H), 7.50 (d, J=8.2 Hz, 1H), 7.39 (t, br., J=7.6 Hz, 1H), 7.06 (s, br., 2H), 6.69 (s, br., 1H), 5.58 (s, br., 1H), 2.35 (s, 3H), 2.21 (m, 3H), 1.74 (s, 3H), 1.65 (s, 3H), 2.6-0.8 (m, 45H) ppm. IR (ATR) λ$^{-1}$=2921 (vs), 2847 (s), 1443 (m), 1361 (m), 1309 (m), 1259 (w), 1005 (w), 848 (m), 748 (m) cm$^{-1}$.

Example 8

Preparation of dichlorobis(tricyclohexylphosphane)(2-furylmethylidene)ruthenium(II) (8)

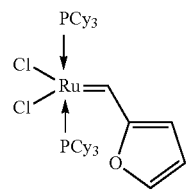

Ru(cod)Cl$_2$ (5.6 g, 20 mmol) was suspended in iPrOH (200 ml) under an Ar atmosphere. DBU (6.6 ml, 44 mmol) and PCy$_3$ (12.34 g, 44 mmol) were added. The brown suspension obtained was stirred at 80° C. for 1 hour. THF (100 ml) was then added and the mixture was stirred at 80° C. for a further 30 minutes. The reaction mixture was then cooled to 10° C. and HCl solution (c=2 M in Et$_2$O, 24 ml) was added. After stirring for 5 minutes, trimethylsilylacetylene (8.3 ml, 60 mmol) was added to the reaction mixture and the mixture was stirred for 20 minutes. 2-Vinylfuran (9.4 g, 100 mmol) was subsequently added. After stirring in an ice bath for 3 hours, the complex 8 was isolated as a dark violet solid, washed thoroughly with cold methanol and dried under reduced pressure. Yield: 13.9 g (85%)

NMR in CDCl$_3$ δ $^{31}$P 37.03 ppm; $^1$H δ 18.79 (s, 1H), 8.12 (s, br., 1H), 7.74 (s, br., 1H), 6.43 (dd, J=3.58 Hz, J=1.74 1H), 2.64 (m, 6H), 1.81-1.67 (m, 33H), 1.48-1.41 (m, 12H), 1.27-1.14 (m, 21H) ppm

Example 9

Preparation of dichloro(thien-2-ylmethylidene)(1,3-bis(2,4,6-trimethylphenyl)imidazol-2-ylidene]-(tricyclohexylphosphane)ruthenium(II) (9)

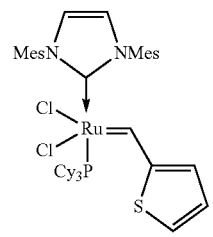

The 1,3-bis(2,4,6-trimethylphenyl)imidazolin-2-ylidene solution (16 mmol in 52 ml of toluene) was added to a solution of complex 4 (8.3 g, 10 mmol) in toluene (400 ml) under an argon atmosphere. The reaction mixture was stirred at room temperature for 4 hours and subsequently washed with water (2×100 ml). The organic phase was admixed with 50 ml of heptane and concentrated by evaporation. Filtration, washing with hexane and subsequently with methanol and drying under reduced pressure gave the product 9 (6.14 g, 72%) as a dark violet solid.

NMR in CDCl$_3$ δ $^{31}$P 31.00 (40%) and 30.65 (60%) ppm; $^1$H δ=18.63 and 18.52 (s, 1H), 8.65 and 7.78 (br. s, 1H), 7.45 and 6.73 (br. s, 1H), 7.04 and 7.00 (br. s, 2H), 6.98 (s, 1H), 6.97 (s, 1H), 6.83 and 6.80 (br. s, 2H), 6.10 and 6.08 (br. s, 1H), 2.51 (s, 3H), 2.34 (s, 6H), 2.27 (m, 6H), 2.08 (s, 3H), 1.96 and 1.90 (br. s, 3H), 1.60-0.85 (m, 30H) ppm Example 10

Preparation of dichloro(thien-2-ylmethylidene)[1,3-bis(2,4,6-trimethylphenyl)-4,5-dimethylimidazol-2-ylidene](tricyclohexylphosphane)ruthenium(II) (10)

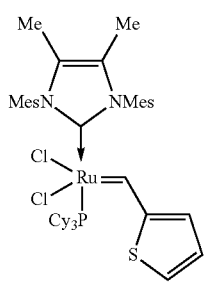

The 4,5-dimethyl-1,3-bis(2,4,6-trimethylphenyl)imidazolin-2-ylidene solution (16 mmol in 52 ml of toluene) was added to a solution of complex 4 (8.3 g, 10 mmol) in toluene (400 ml) under an argon atmosphere. The reaction mixture was stirred at room temperature for 4 hours and subsequently washed with water (2×100 ml). The organic phase was admixed with 50 ml of heptane and concentrated by evaporation. Filtration, washing with hexane and subsequently with methanol and drying under reduced pressure gave the product 10 (4.74 g, 54%) as a dark violet solid.

NMR in CDCl$_3$ δ $^{31}$P 30.16 (37%) and 29.65 (63%) ppm; $^1$H δ=18.64 and 18.52 (br. s, 1H), 8.66 and 7.76 (br. s, 1H), 7.42 and 6.72 (br. s, 1H), 7.03 and 6.99 (br. s, 2H), 6.82 and 6.79 (br. s, 2H), 6.07 and 6.05 (br. s, 1H), 2.45 (s, 3H), 2.34 (s, 3H), 2.26 (m, 9H), 2.07 (s, 3H), 1.88 and 1.83 (s, 3H), 1.74 (s, 3H), 1.71 (s, 3H), 1.60-0.85 (m, 30H) ppm.

Example 11

Preparation of dichloro(thien-2-ylmethylidene)(1,3,4-triphenyl-4,5-dihydro-1H-1,2,4-triazol-5-ylidene)(tricyclohexylphosphane)ruthenium(II) (11)

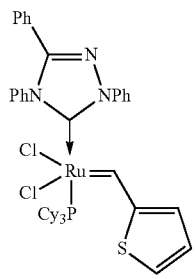

1,3,4-Triphenyl-4,5-dihydro-1H-1,2,4-triazol-5-ylidene (450 mg, 1.5 mmol) was added to a solution of complex 4 (829 mg, 1 mmol) in dried toluene (20 ml) and the mixture was stirred overnight at room temperature under an argon atmosphere. The reaction mixture was evaporated under reduced pressure and admixed with hexane (15 ml). The precipitated solid was filtered off, washed thoroughly with cold hexane and dried under reduced pressure. Yield: 662 mg (78%).

NMR in CDCl$_3$ δ $^{31}$P 26.64 (40%) and 26.03 (60%) ppm; $^1$H δ=18.66 (J=5.07 Hz) and 18.47 (J=3.0 Hz) (br. d, 1H), 8.56 and 7.85 (br. d, J=6 Hz, 1H), 8.18 (d, J=7.52 Hz, 1H), 7.8-7.1 (m, 16H), 2.17 (br. m, 3H), 1.7-1.05 (br. m, 30H) ppm Example 12

Preparation of dichlorobis(tricyclohexylphosphane)(1-cyclohexenylmethylidene)ruthenium(II) (12)

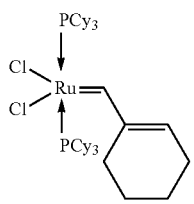

Complex 1 (761 mg, 1 mmol) was added to a cooled solution of 1-vinylcyclohexene (648 mg, 6 mmol) in dried THF (5 ml) and the mixture was stirred overnight at 4° C. under an argon atmosphere. The reaction mixture was admixed with MeOH (30 ml). The precipitated solid was filtered off, washed thoroughly with cold MeOH and dried under reduced pressure. Yield: 410 mg (50%).

NMR in C$_6$D$_6$ δ $^{31}$P 36.32 ppm; $^1$H δ=19.08 (s, 1H), 7.21 (s, 1H), 2.87 (m, 2H), 2.60 (m, 6H), 1.95-1.11 (m, 66H) ppm

Example 13

Preparation of dichlorobis(tricyclohexylphosphane) (1-cyclopentylmethylidene)ruthenium(II) (13)

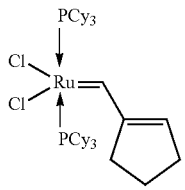

Complex 1 (761 mg, 1 mmol) was added to a cooled solution of 1-vinylcyclopentene (470 mg, 5 mmol) in dried THF (5 ml) and the mixture was stirred overnight at 4° C. under an argon atmosphere. The reaction mixture was admixed with MeOH (30 ml). The precipitated solid was filtered off, washed thoroughly with cold MeOH and dried at reduced pressure. Yield: 350 mg (43%).

NMR in $C_6D_6$ δ $^{31}$P 37.26 ppm; $^1$H δ=19.30 (s, 1H), 6.97 (s, 1H), 3.14 (m, 2H), 2.60 (m, 6H), 1.95-1.11 (m, 64H) ppm

Example 14

Ring Closing Metathesis of N,N-diallyl-p-toluenesulfonamide

A solution of N,N-diallyl-p-toluenesulphonamide (0.350 mmol, 84 mg) in 17.5 ml of toluene was admixed with an Ru-carbene complex according to the invention as the catalyst under argon and stirred at 80° C. Here, argon was introduced directly into the reaction mixture through a capillary. 200 μl of an aliquot of reaction solution were added to 500 μl of 2M ethyl vinyl ether solution in methylene chloride and analysed by means of GC.

In the presence of complex 4 (0.1 mol %), a conversion of 93% was observed after 15 minutes.

In the presence of complex 5 (0.1 mol %), a conversion of 99% was observed after 40 minutes.

In the presence of complex 6 (0.05 mol %), a conversion of 98% was observed after 40 minutes.

Example 15

Ring Closing Metathesis of Diethyl Diallylmalonate

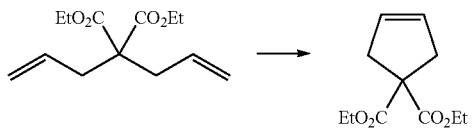 [SMILES: C=CCC(CC=C)(C(=O)OCC)C(=O)OCC ; CCOC(=O)C1(C(=O)OCC)CC=CC1]

A solution of diethyl diallylmalonate in dichloromethane (c=3M) was admixed with 0.1 mol % of catalyst 5 under argon and stirred at 40° C. 200 μl of an aliquot of reaction solution were added to 500 μl of 2M ethyl vinyl ether solution in methylene chloride and analyzed by means of GC. In the presence of complex 5, a conversion of 99% was observed after 3 hours.

Example 16

Ring Closing Metathesis of N,N-dimethallyl-p-toluene-sulfonamide

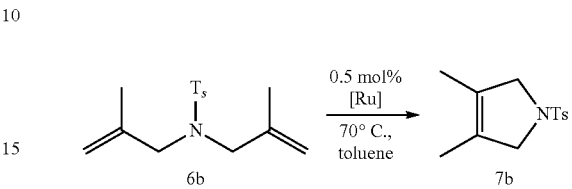

A solution of N,N-dimethallyl-p-toluenesulfonamide (2 mmol, 559 mg) in 100 ml of toluene was admixed with the Ru-carbene complex according to the invention as catalyst under argon and stirred at 80° C. Here, argon was introduced directly into the reaction mixture through a capillary. 200 μl of an aliquot of reaction solution were added to 500 μl of 2M ethyl vinyl ether solution in methylene chloride and analyzed by means of GC.

In the presence of complex 7 (0.5 mol %), a conversion of 70% was observed after 10 minutes.

The invention claimed is:

1. A process for preparing ruthenium complexes of the general formula (I)

$$RuX_2(=CH—CH_2R)L_2 \qquad (I),$$

wherein

X is an anionic ligand,

R is hydrogen or a ($C_1$-$C_{18}$)-alkyl, ($C_3$-$C_8$)-cycloalkyl, ($C_2$-$C_7$)-heterocycloalkyl, ($C_6$-$C_{14}$)-aryl or ($C_3$-$C_{14}$)-heteroaryl radical and L is selected from the group consisting of phosphanes, phosphinites, phosphonites and phosphites, which comprises A) reacting an Ru metal salt of the general formula (II):

$$RuX_xN_y \qquad (II),$$

wherein x is an integer greater than or equal to 2 and

X is as defined above, y is an integer greater than or equal to 0 and y>=1;

the ligands N are identical or different coordinating uncharged ligands;

with L in the presence of a base and a reducing agent and

B) subsequently reacting with a silylalkyne of the general formula III $$R—C≡CSiR'_3 \qquad (III),$$

wherein

R is as defined above, the radicals R' are identical or different radicals which can be selected from the group consisting of hydrogen, ($C_1$-$C_8$)-alkyl, ($C_1$-$C_8$)-alkoxy, ($C_6$-$C_{10}$)-aryloxy, ($C_6$-$C_{10}$)-aryl.

2. A process for preparing ruthenium complexes of the general formula $$RuX_2(=R^1R^2)L_2,$$

where
X is an anionic ligand,
L is selected from the group consisting of phosphanes, phosphinites, phosphonites and phosphites,
$R^1$ is hydrogen or a $(C_1-C_{18})$-alkyl or $(C_3-C_8)$-cycloalkyl or $(C_2-C_7)$-heterocycloalkyl, $(C_6-C_{14})$-aryl or $(C_3-C_{14})$-heteroaryl radical and $R^2$ is a $(C_6-C_{14})$-aryl or $(C_3-C_{14})$-heteroaryl radical and the radicals $R^1$ and $R^2$ can have a 5-7-membered ring, which comprises
A) reacting an Ru metal salt of the general formula (II):

$$RuX_xN_y \quad (II),$$

wherein
x is an integer greater than or equal to 2 and
X is as defined above,
y is an integer greater than or equal to 0
and y>=1;
the ligands N are identical or different coordinating uncharged ligands;
with L in the presence of a base and a reducing agent and
B) subsequently reacting with a silylalkyne of the general formula III $$R-C\equiv CSiR'_3 \quad (III),$$

wherein
R and R' have the meanings given in claim 1, and

C) subsequently reacting with an alkene of the general formula IV $$H_2C=CR'R^2 \quad (IV),$$

wherein
$R^1$ and $R^2$ have the meanings given above.

3. The process according to claim 1, wherein L is selected from the group consisting of triphenylphosphane, triisopropylphosphane, tricyclohexylphosphane and 9-cyclohexyl-9-phosphabicyclo[3.3.1]nonane.

4. The process according to claim 1, wherein x=3 and y=0 for the Ru metal salt of the general formula $RuX_xN_y$ and that the reduction of the Ru metal salt is carried out by means of hydrogen in the presence of metallic reducing agent.

5. The process according to claim 3, wherein said reducing agent is magnesium.

6. The process according to claim 1, wherein an excess of basic ligand is used as base.

7. The process according to claim 1, wherein x>=2 and y>0 for the Ru metal salt of general formula $RuX_xN_y$ and that the reduction of the Ru metal salt is carried out by means of alcohol or the formic acid-triethylamine complex.

8. The process according to claim 7, wherein said reducing agent is a secondary alcohol.

9. The process according to claim 1, wherein said base is an amine.

10. The process according to claim 9, wherein said base is triethylamine or 1,8-diazobicyclo[5.4.0]undec-7-ene.

11. The process according to claim 2, wherein L is selected from the group consisting of triphenylphosphane, triisopropylphosphane, tricyclohexylphosphane and 9-cyclohexyl-9-phosphabicyclo[3.3.1]nonane.

* * * * *